US00PP25659P3

(12) United States Plant Patent
Reardon

(10) Patent No.: US PP25,659 P3
(45) Date of Patent: Jun. 30, 2015

(54) ***ILEX* PLANT NAMED 'CENTENNIAL DRAGON'**

(50) Latin Name: *Ilex×meserveae (I. centrochinensis×I. aquifolium)*
Varietal Denomination: Centennial Dragon

(71) Applicant: Reardon Nursery, Inc., Boring, OR (US)

(72) Inventor: Michael D. Reardon, Boring, OR (US)

(73) Assignee: Reardon Nursery, Inc., Boring, OR (US)

( * ) Notice: Subject to any disclaimer, the term of this patent is extended or adjusted under 35 U.S.C. 154(b) by 187 days.

(21) Appl. No.: 13/986,988

(22) Filed: Jun. 20, 2013

(65) Prior Publication Data

US 2014/0380538 P1 Dec. 25, 2014

(51) Int. Cl.
*A01H 5/02* (2006.01)

(52) U.S. Cl.
USPC ..... Plt./247

(58) Field of Classification Search
USPC ..... Plt./247
See application file for complete search history.

*Primary Examiner* — Susan McCormick Ewoldt
(74) *Attorney, Agent, or Firm* — Klarquist Sparkman, LLP

(57) ABSTRACT

A new and distinct cultivar of *Ilex* plant characterized by its naturally pyramidal habit, shiny, rich plum brown new growth that holds the dark coloration through the season in two or three flushes of new growth, mite resistance, and deep green, satiny mature foliage with soft spines that don't catch your clothing, profuse and long lasting bright red berries, and good cold tolerance.

5 Drawing Sheets

Botanical classification: *Ilex×meserveae* (*I. centrochinensis×I. aquifolium*).

Variety nomination: 'Centennial Dragon'.

Parentage: branch mutation of *Ilex* 'Centennial Girl'.

FIELD

The present invention relates to a new and distinct cultivar of an evergreen shrub of *Ilex×meserveae* and given the name 'Centennial Dragon'. The genus *Ilex* is of the family Aquifoliaceae.

BACKGROUND

The new cultivar was found as a branch mutation of *Ilex* 'Centennial Girl', U.S. Plant Pat. No. 10,750, at a nursery in Boring, Oreg. *Ilex* 'Centennial Dragon' is unique for:

1) its shiny plum brown new growth that holds the dark coloration through the season in two or three flushes of new growth,
2) its naturally pyramidal habit that doesn't need pruning to hold its density,
3) deep green, satiny, mature foliage with soft spines that don't catch your clothing.

In addition *Ilex* 'Centennial Dragon' has profuse and long lasting bright red berries and good cold tolerance.

Compared to the parent plant, *Ilex* 'Centennial Girl', an unpatented plant, *Ilex* 'Centennial Dragon' has rich shiny plum brown new growth rather than always green new growth. *Ilex* 'Centennial Dragon' is slightly more upright and faster growing than *Ilex* 'Centennial Girl'.

Compared to *Ilex* 'Dragon Lady', an unpatented plant, *Ilex* 'Centennial Dragon' has leaves that have more but much softer spines. Softer spines mean that the leaves do not catch your clothing or cut your hands. *Ilex* 'Centennial Dragon' has denser branching that does not require pruning to grow into a good form in a container like 'Dragon Lady' requires.

Asexual propagation by cuttings in Boring, Oreg., shows that the foregoing characteristics and distinctions come true to form and are established and transmitted through succeeding propagations. The present invention has not been evaluated under all possible environmental conditions. The phenotype may vary with changes in environment without a change in the genotype of the plant.

SUMMARY

The foregoing and other objects, features, and advantages of the invention will become more apparent from the following detailed description, which proceeds with reference to the accompanying figures.

DETAILED DESCRIPTION

Figure 1:
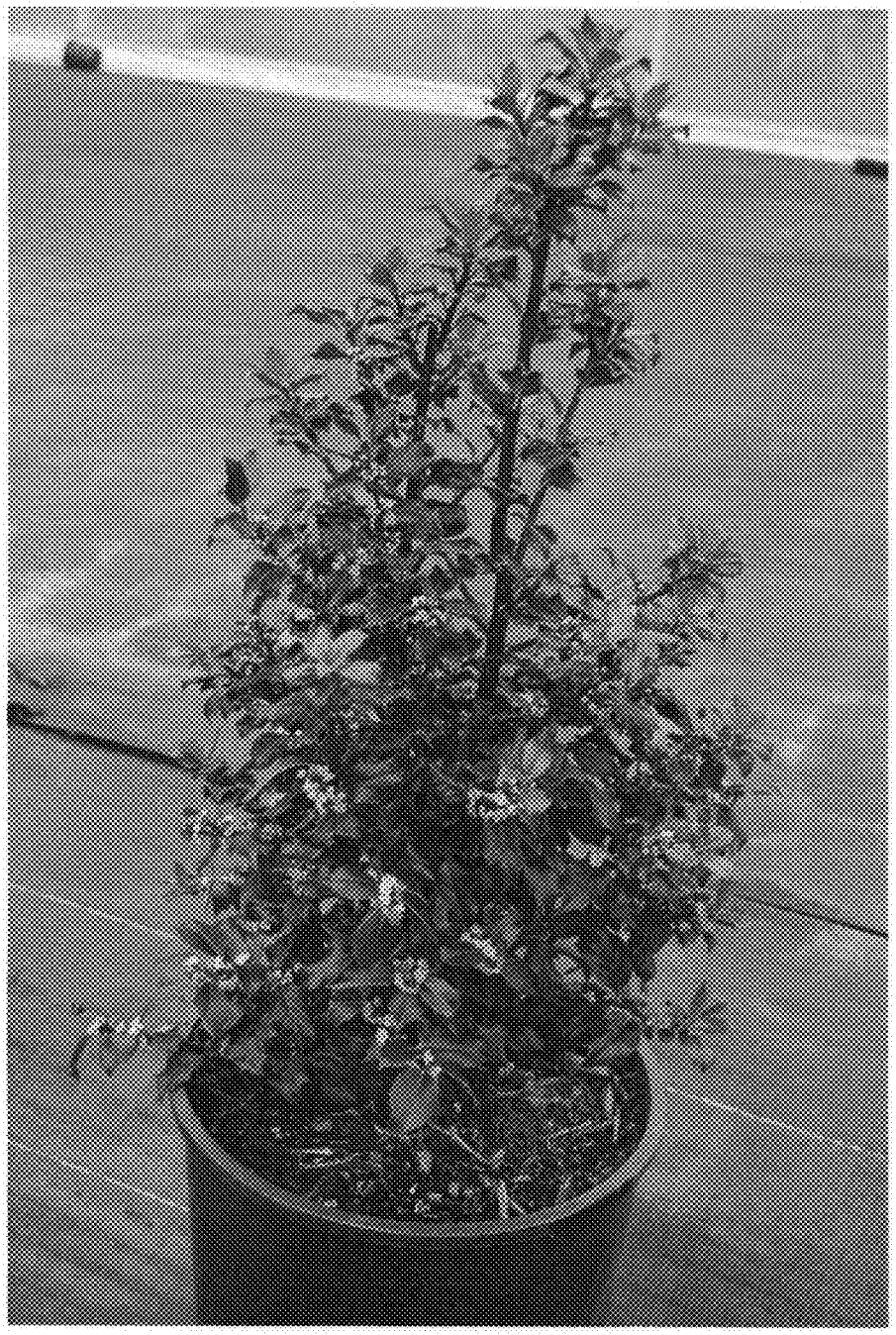
FIG. 1 shows a 4 year old plant of the new cultivar growing in a 5 gallon container in flower and winter foliage in April in Canby, Oreg.
Figure 2:
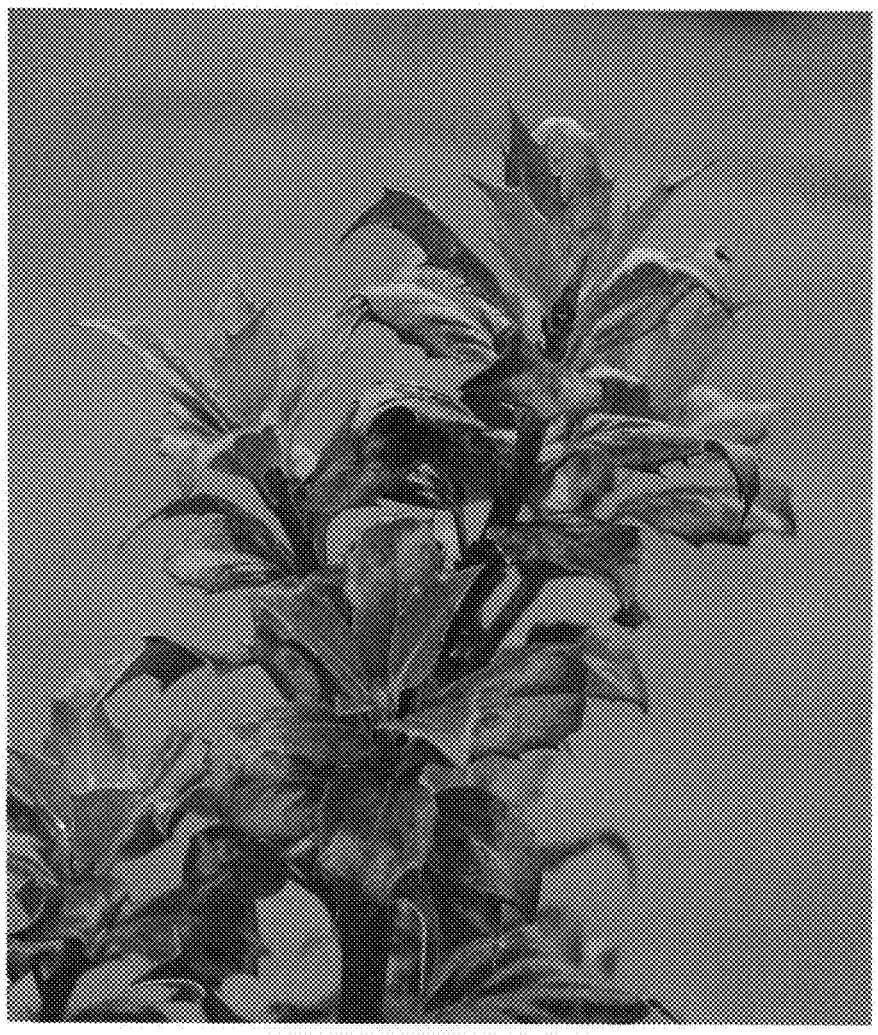
FIG. 2 shows a close up of the winter leaves.
Figure 3:
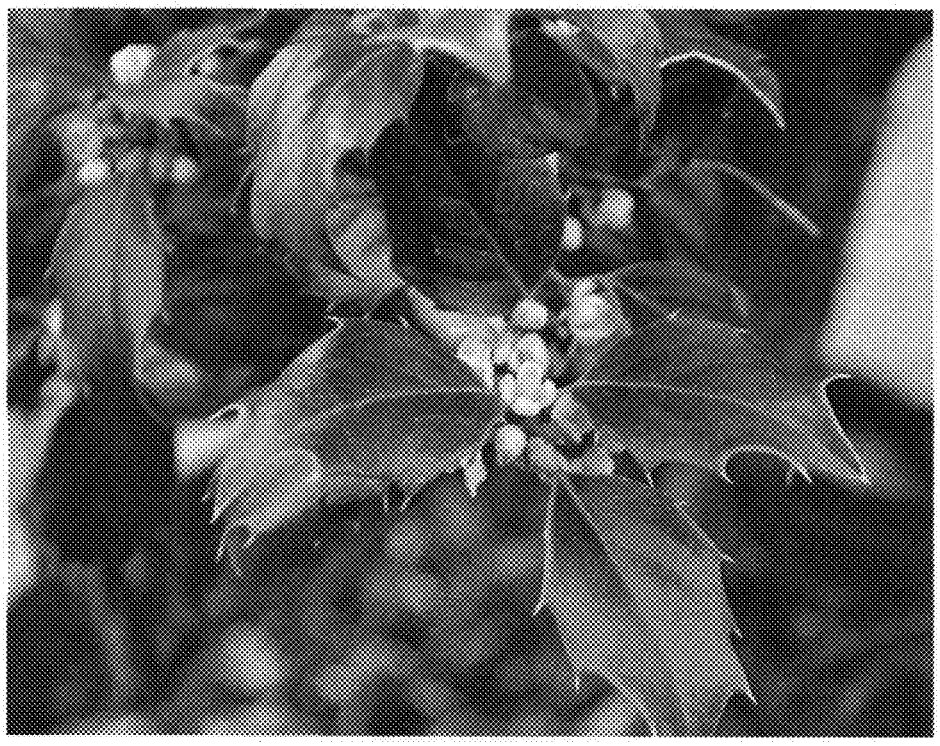
FIG. 3 shows a close up of a flowering branch.
Figure 4:
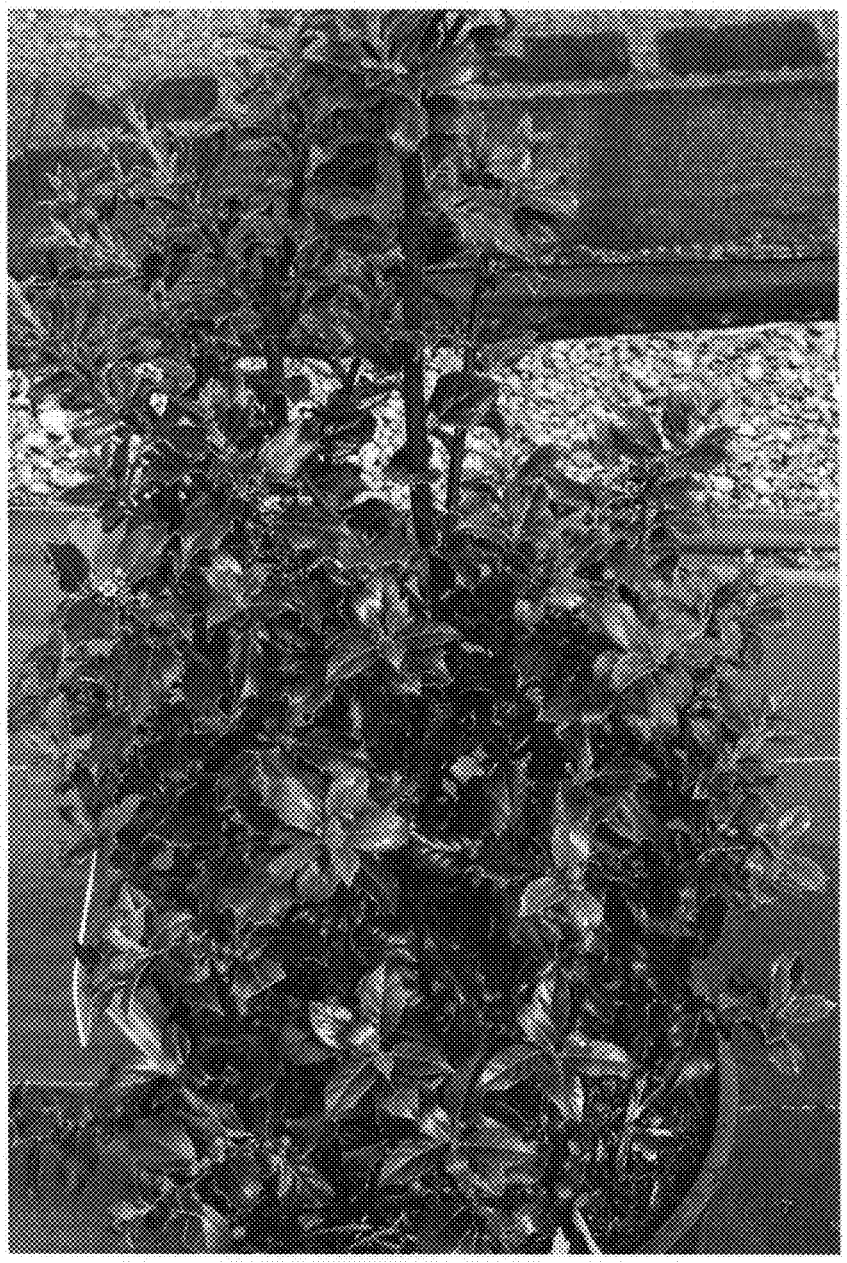
FIG. 4 shows the same 4 year old plant growing in a 5 gallon with spring new growth.
Figure 5:
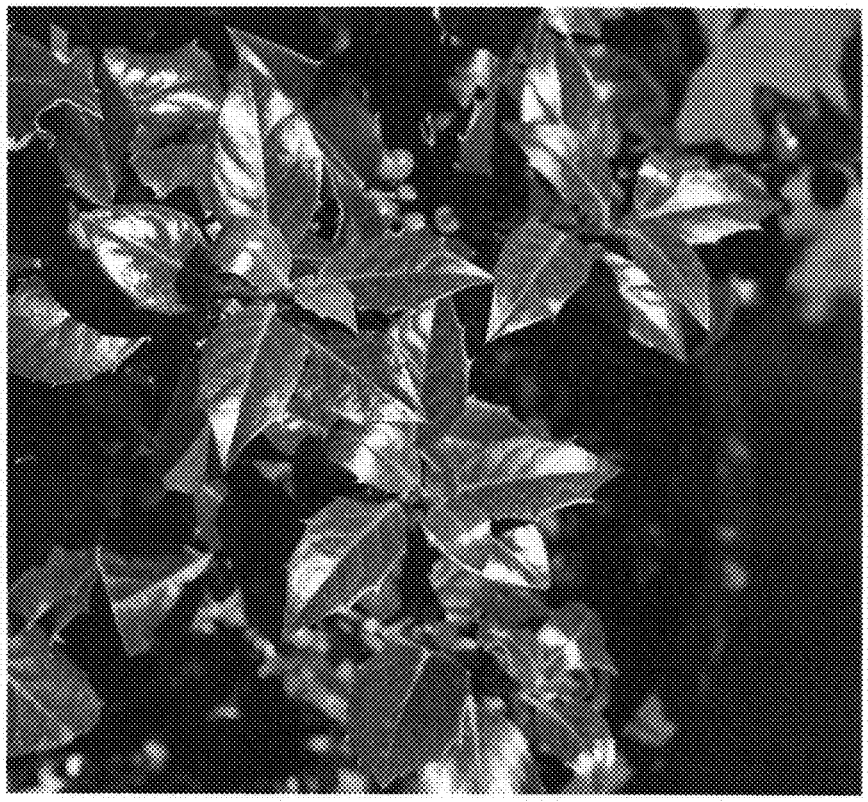
FIG. 5 shows a close up of the new spring growth.

The following is a detailed description of the new cultivar based on observations taken in early April of a four-year-old specimen grown in a 5 gallon container in full sun in Boring, Oreg. Boring, Oreg. is in USDA hardiness zone 7. The color descriptions are all based on *The Royal Horticultural Society Colour Chart*, 5$^{th}$ edition, 2007.

Plant:

*Type*.—Evergreen shrub.

*Hardiness*.—USDA Zones 6 to 9.

*Size*.—64 cm tall and 36 cm wide (A mature shrub grows to 1.8 to 2.4 m wide and 4.7 to 6 m tall).

*Growth habit*.—Upright, dense, pyramidal.

Stem:

*Type*.—Woody.

*Size*.—Trunk base is 2 cm at 1 cm above the ground.

*Surface*.—One year old stems are densely pubescent, 2 year and older stems are glabrous.

*Vigor*.—Excellent.

*Rooting*.—From current season's wood takes 60 to 90 days to root.

*Color*.—Young 1 to 3 year old stems are Brown 200A in sun to Yellow Green 147A in shade, 4 year and older stems are Greyed Green 197A with Yellow Green 147A between striations.

Leaf:

*Type*.—Simple, leaves cup back slightly.

*Shape*.—Elliptic in first year leaves and ovate in mature 2 year and older leaves.

*Arrangement*.—Alternate.

*Margins*.—Toothed.

*Apex*.—Aristate.

*Base*.—Cuneate.

*Venation*.—Pinnate, with main vein and base of lateral veins Yellow Green 147B on top and 147C on bottom of mature leaves.

*Blade size*.—Grows to 3 cm long and 2 cm wide on first years leaves, mature leaves grow to 4.5 cm long and 3 cm wide.

*Texture*.—Leathery.

*Surface*.—Top side glossy and glabrous, bottom side glabrous.

*Petiole description*.—5 mm long and 1 mm wide, pubescent on first year leaves, Yellow Green 148C.

*Color*.—New leaves topside Brown 200A with the main vein Yellow Green 147C, bottom side Greyed Green 197A with the main vein Yellow Green 147C; one year old leaves topside Yellow Green 147B with tints of Brown 200A or 200B, bottom side Yellow Green 147C; mature leaves topside Green 139A, bottom side Yellow Green 147B.

Inflorescence:

*Type*.—Fascicle in axils of two year old leaves.

*Dimensions of fascicle*.—18 mm wide by 13 mm deep.

*Number of flowers per fascicle*.—4 to 7.

*Peduncle*.—None.

*Pedicel description*.—3 to 4 mm long, 1 mm wide, pubescent, Yellow Green 146C.

*Bloom period*.—Early April in Boring, Oreg.

Flower bud:

*Size*.—4 mm wide and 3 mm long.

*Description*.—Ovoid.

*Color*.—Yellow Green 145D.

Flower:

*Type*.—Regular.

*Description*.—4 cm deep and 7 cm wide overall, rotate in shape, 4 petals, each oblong, 3 mm wide and 4 mm long, cupped at the tip, margin entire, tip obtuse, base truncate, both sides glabrous, topside White NN155A, bottom side White NN155A with Yellow Green 145D at the tip; 4 sepals, 1 mm long and 1.5 mm wide, triangular in shape, margin entire, tip acute, Brown 200A and mostly glabrous on both sides; 4 stamen, White NN155C, 3 mm long, filaments about 3 mm long, stamen reduced and without pollen, less than 0.5 mm long; pistil and ovary 3 mm long and 2.2 mm wide, ovoid, Yellow Green 146C overall, style and stigma 0.5 mm long and 1 mm wide.

*Fragrance*.—None.

Fruit: A drupe, round, very abundant, in clusters of six usually, approximately 6 to 8 mm. in diameter, globose to sub-globose, color closest to Red 45A.

Seed: Not seen.

Pest and disease tolerance: Plants of *Ilex* 'Centennial Dragon' have the same pest and disease tolerance as *Ilex* 'Centennial Girl'.

I claim:

1. A new and distinct *Ilex* plant as herein illustrated and described.

* * * * *